United States Patent [19]

Larose

[11] Patent Number: 5,531,756
[45] Date of Patent: Jul. 2, 1996

[54] ARTHROSCOPIC SURGICAL PUNCH

[76] Inventor: Daniel J. Larose, 1408 Skyline Dr., Council Bluffs, Iowa 51503

[21] Appl. No.: 284,110

[22] Filed: Aug. 2, 1994

[51] Int. Cl.⁶ .................................................. A61B 17/32
[52] U.S. Cl. ........................ 606/184; 606/174; 128/751
[58] Field of Search .................................. 606/184, 170, 606/174, 207; 128/751, 754; 30/229, 363, 364, 304, 305

[56] References Cited

U.S. PATENT DOCUMENTS

| | | |
|---|---|---|
| D. 289,437 | 4/1987 | Honkanen . |
| 2,778,357 | 1/1957 | Leibinger et al. ........................ 606/184 |
| 2,994,321 | 8/1961 | Tischler . |
| 4,043,343 | 8/1977 | Williams . |
| 4,433,687 | 2/1984 | Burke et al. . |
| 4,662,371 | 5/1987 | Whipple et al. . |
| 4,712,545 | 12/1987 | Honkanen . |
| 5,211,655 | 5/1993 | Hasson . |
| 5,217,479 | 6/1993 | Shuler . |
| 5,254,129 | 10/1993 | Alexander . |
| 5,303,472 | 4/1994 | Mbanugo ........................ 30/124 |

FOREIGN PATENT DOCUMENTS

WO94/27512  12/1994  WIPO .................... 606/184

*Primary Examiner*—Michael H. Thaler
*Assistant Examiner*—Mark S. Leonardo

[57] ABSTRACT

A surgical punch for cutting body tissue, comprises an axially elongated support having first and second end portions; first and second cutting jaws operably associated with the first end portion and movable between an open position and a closed position relatively toward and closely past each other in tissue-severing shearing action; an actuator operably associated with the second end portion for providing relative motion between the first and second jaws; and a plurality of upstanding blades disposed within the opening for dividing the opening into a plurality of smaller openings. The first jaw has an opening adapted to receive the second jaw in tissue-severing action in the closed position. The second jaw cooperates with the blades when in the closed position, thereby to cut the tissue into smaller fragments substantially corresponding to the sizes of the smaller openings.

21 Claims, 3 Drawing Sheets

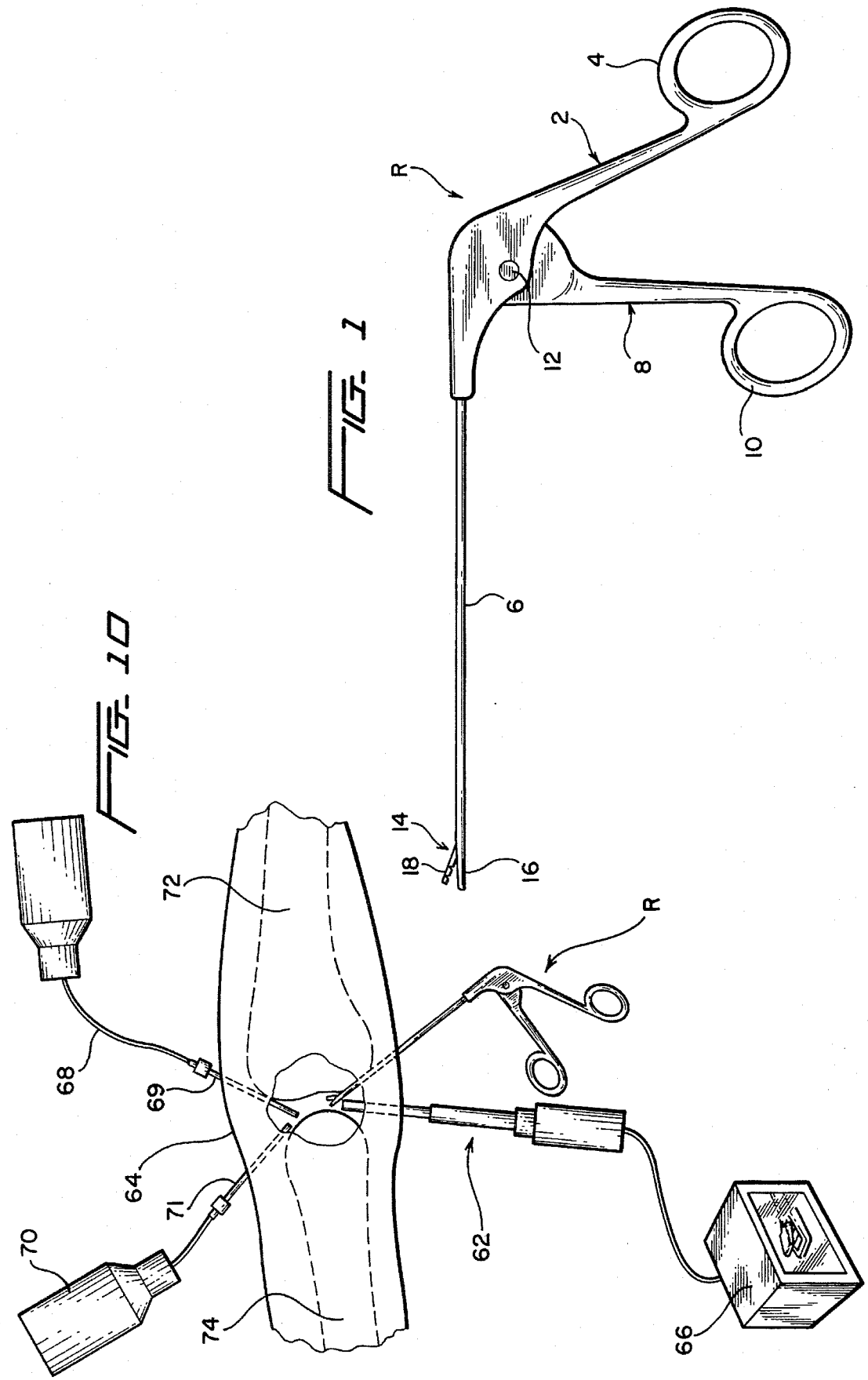

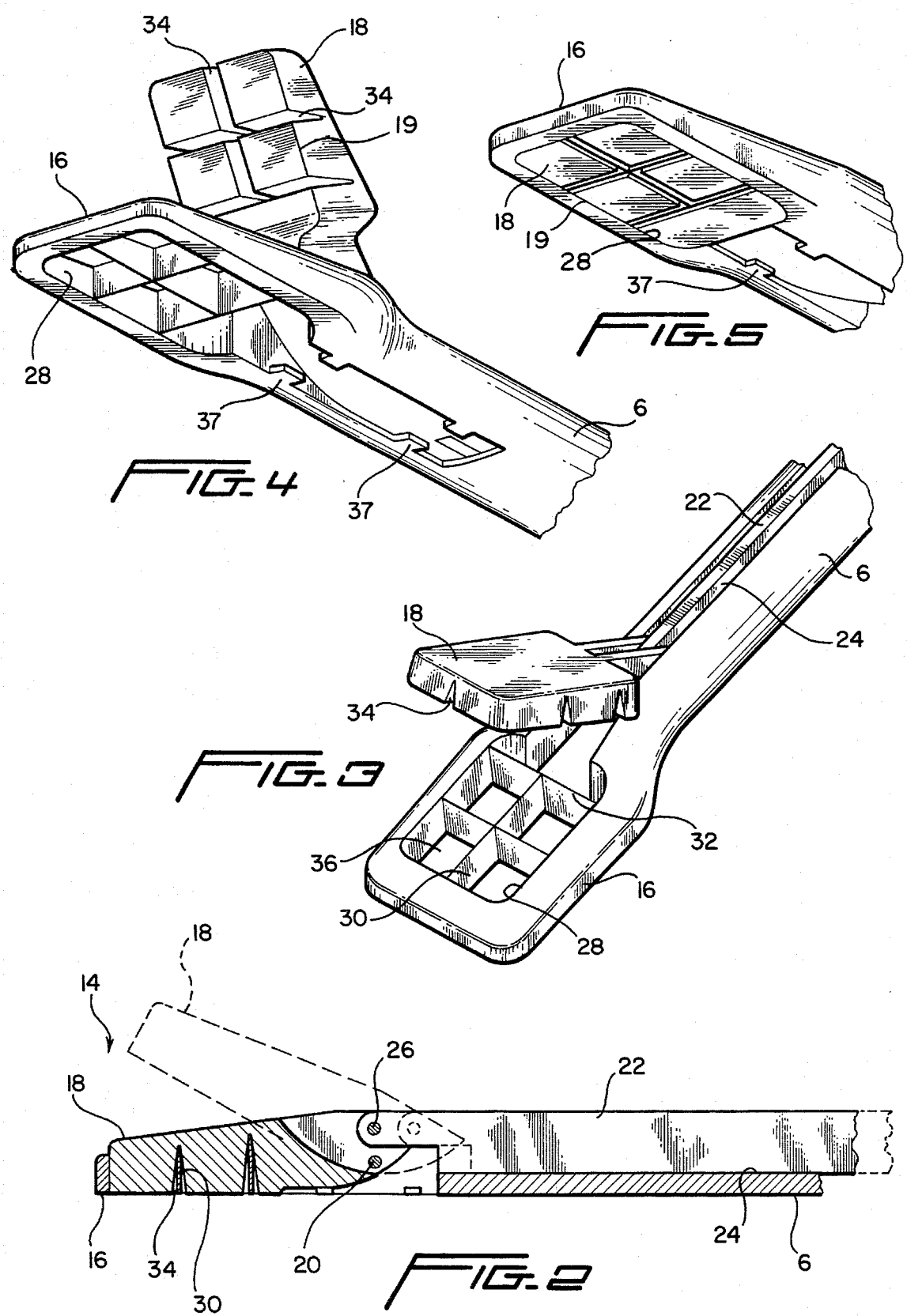

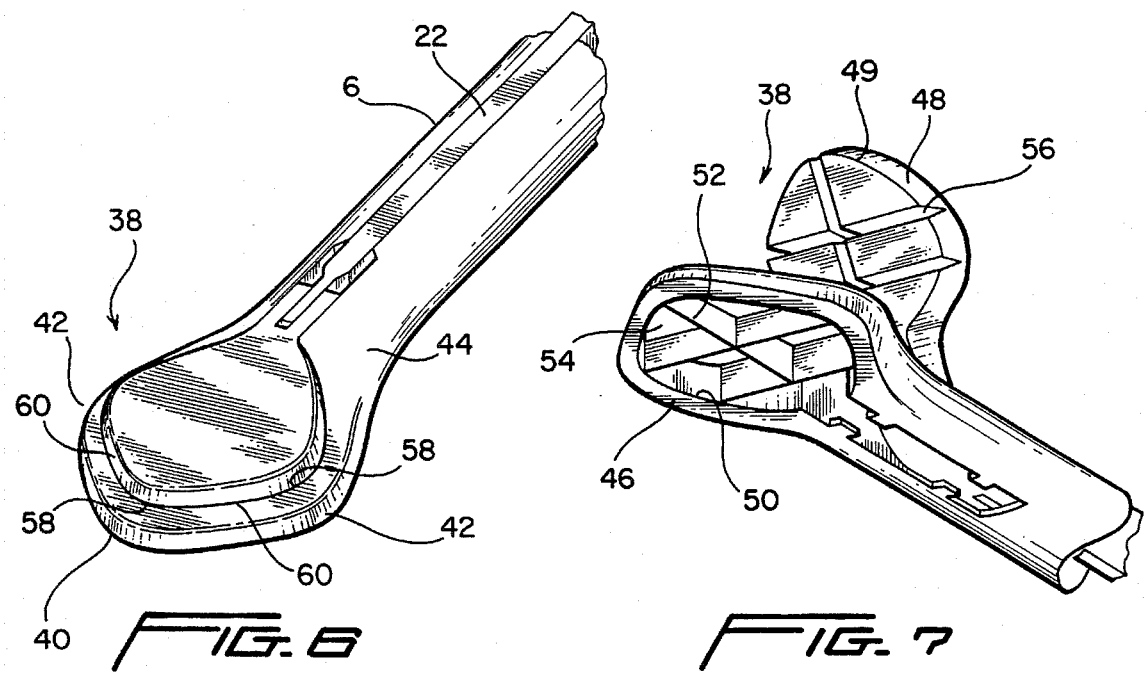
FIG. 6
FIG. 7
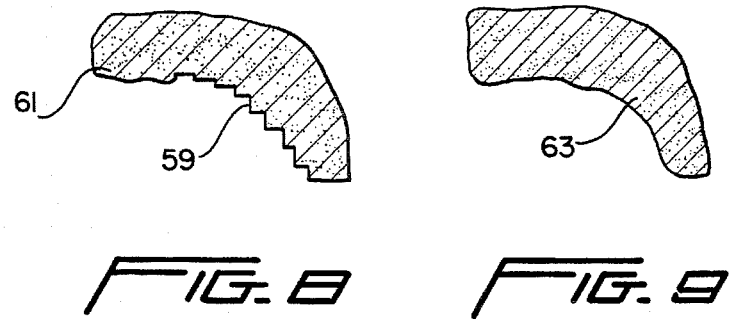
FIG. 8
FIG. 9

ARTHROSCOPIC SURGICAL PUNCH

FIELD OF THE INVENTION

The present invention relates generally to a surgical punch and specifically to an arthroscopic surgical punch typically used in knee surgery.

BACKGROUND OF THE INVENTION

Arthroscopic surgery is an orthopaedic technique consisting of introducing a fiber optic pen-like instrument into a joint, most commonly the knee, to provide a visual image of the surgery site to a video monitor which the surgeon watches to control his instruments within the knee. One of the most common procedures is a meniscectomy, consisting of removing fragments of broken cartilage in the knee, using a surgical cutting instrument called a punch. Arthroscopic surgery is done under a water medium provided by cannulas to pump water into the knee and to outflow the water therefrom.

Punches available today are usually square-shaped and usually cut only one fragment. If the fragments are too big, sometimes the cannulas will get clogged and will need to be cleaned, which wastes valuable surgical time. Another instrument used in meniscectomy is a suction shaver, which is a mechanical instrument which bites and suctions pieces of cartilage. Fragments made from using a prior art punch can sometimes plug the suction shaver. An example of a suction shaver is disclosed in U.S. Pat. No. 5,217,479.

Inflow and outflow cannulas that are inserted above the kneecap can be made larger to accommodate larger fragments generated by prior art punches. However, it is more practical to make cannulas smaller. It is less traumatic for the knee.

Suction shaver used in meniscectomy is typically small in diameter because of the limited space between the femur and the tibia where the instrument is inserted. Additionally, some knees are tight and the maximum suction shaver outside diameter that can be used is about 3.5 mm. If a larger suction shaver is used, the articular cartilage could be damaged, which would be poor surgical technique. Thus, a prior art punch used in this area would typically clog the suction shaver.

There is therefore a need for an arthroscopic surgical punch that will solve the above problems.

OBJECTS AND SUMMARY OF THE INVENTION

It is an object of the present invention to provide a surgical punch that will make smaller fragments thereby to minimize clogging of the cannulas and suction shavers used in the operation.

It is another object of the present invention to provide a surgical punch that minimizes the size of the cannulas and suction shavers used in the operation, thereby minimizing trauma to the knee.

It is still another object of the present invention to provide a surgical punch that will generate fragments that will minimize or eliminate clogging of the cannulas and suction shaver used in surgery to the meniscus located between the femur and tibia, especially when a bent suction shaver is used, which technically cannot be taken apart during surgery to unclog it.

It is yet another object of the present invention to provide a surgical punch with an arrow-triangular-shaped tip that provides easier penetration into the knee.

It is still another object of the present invention to provide a surgical punch with an arrow-triangular-shaped tip that can take round cuts on the edges of the meniscus.

In summary, the present invention provides a surgical punch that generates smaller fragments of tissue and having a tip that can relatively easily penetrate the knee and provide arcuate bites, thereby permitting a better partial meniscectomy.

These and other objects of the present invention will become apparent from the following detailed description.

BRIEF DESCRIPTION OF THE DRAWINGS

FIG. 1 is a side elevational view of a surgical punch made in accordance with the present invention.

FIG. 2 is an enlarged fragmentary cross-sectional view through the cutting tip of the punch of FIG. 1, the phantom lines showing the movable jaw in the open position.

FIG. 3 is a fragmentary top perspective view of one embodiment of a cutting tip made in accordance with the present invention, showing the movable jaw in the open position.

FIG. 4 is a fragmentary bottom perspective view of the tip of FIG. 3.

FIG. 5 is a fragmentary bottom perspective view of the tip of FIG. 3 shown in the closed position.

FIG. 6 is a fragmentary top perspective view of another embodiment of a cutting tip made in accordance with the present invention, showing the movable jaw in the closed position.

FIG. 7 is a fragmentary bottom perspective view of the tip of FIG. 6, showing the movable jaw in the opened position.

FIG. 8 is a schematic view of a cartilage cut with the tip of FIG. 3.

FIG. 9 is a cartilage cut with the tip of FIG. 6.

FIG. 10 is a schematic fragmentary view of a knee undergoing arthroscopic surgery using the punch of FIG. 1.

DETAILED DESCRIPTION OF THE INVENTION

A surgical punch R using the present invention is disclosed in FIG. 1. The punch R comprises an arm 2 with a finger hole 4 and an axially elongated support or shank 6 secured to the arm 2. Another arm 8 with a finger hole 10 is pivotally secured to the arm 2 at pivot 12.

The punch R has a cutting tip 14 disposed at the end portion of the shank 6. The tip 14 comprises a fixed jaw 16 and a movable jaw 18. The movable jaw 18 is operably connected to the arm 8 such that pivoting of the arm 8 about the pivot 12 causes opening and closing of the jaw 18 relative to the jaw 16 in a tissue-severing shearing action.

The movable jaw 18 is pivotably secured to the lower jaw 16 at pivot 20, as best shown in FIG. 2. A coupling member 22 disposed within a longitudinal groove 24 in the support 6 is pivotably secured to the movable jaw 18 at pivot 26, which is offset with respect to the pivot 20. The other end of the coupling member 22 is operably secured to the arm 8 and adapted to push and pull the member 22 and thereby close and open the jaw 18 as the arm 8 is pivoted about the pivot 12.

The tip 14 is generally rectangular in shape, as best shown in FIGS. 3, 4 and 5. The tip 14 is wider than the width of the shank 6. The fixed jaw 16 has an opening 28 adapted to receive the movable jaw 18 closely in a tissue-severing shear action. The movable jaw 18 has an outer periphery 19 that is adapted to be to be received within the opening 28 in the closed position to provide the tissue-severing shearing action, as best shown in FIG. 2. A plurality of upstanding blades 30 are disposed within the opening 28 in grid-like fashion, as best shown in FIG. 3. The blades 30 have cutting edges 32 that are disposed toward the movable jaw 18. The movable jaw 18 includes a plurality of slots 34 that mate and receive the corresponding blades 30 when in the closed position, as best shown in FIGS. 2 and 5. Thus, the slots 34 are arranged in the same grid-like configuration as the blades 30, as best shown in FIGS. 4 and 5. The blades 30 divide the opening 28 into a plurality of smaller openings or grids 36. A person of ordinary skill in the art will understand that the tissue fragments generated from the cutting tip 14 will be no larger than the size of one grid or cell 36 defined by the blades 30 and the sides of the opening 28. The blades 30 are disposed transversely to each other and substantially flush with the opening 28.

The tip 14 is approximately 3.2 mm wide by 5 mm long, divided into four equal quadrants, each measuring approximately 1.6 mm by 2.5 mm. The suction shaver (not shown) used for meniscectomy has a typical inside opening of 2.7 mm. Thus, the tissue fragments generated by the punch R will not clog the suction shaver.

The cutting tip 14 is advantageously tapered from wide to narrow towards the distal end of the tip for relatively ease of insertion into the knee, as best shown in FIG. 2.

Stops 37 provide the limit of travel for the movable jaw 18 in the closed position, as best shown in FIG. 5.

Another embodiment of cutting tip 38 is disclosed in FIGS. 6 and 7. The cutting tip 38 is substantially arrow-triangular-shaped with a narrow front portion 40, a wider middle portion 42 and a narrow end portion 44, as best shown in FIG. 6. The tip 38 has a fixed jaw 46 and a movable jaw 48 that operates the same way as that disclosed for the tip 14. The fixed jaw 46 has an opening 50 in which is disposed a plurality of blades 52, thereby dividing the opening 50 into a plurality of smaller openings or cells 54, as best shown in FIG. 7. The movable jaw 48 has a plurality of slots 56 that are arranged to mate and receive the blades 52 when the jaw 48 is in the closed position, as similarly shown in FIG. 2 for the tip 14. The movable jaw 48 has an outer periphery 49 adapted to be received within the opening 50 in the closed position to provide the tissue-severing shearing action.

The tip 38 has rounded cutting edges 58 disposed substantially at the front and middle portions of 40 and 42 and somewhat rounded straight cutting edges 60 intermediate of the rounded cutting edges 58, as best shown in FIG. 6. In effect, the cutting tip 38 has a somewhat triangular rounded shape to advantageously provide different shapes of bites on the tissue being cut. The curvature of the cutting edges 58 is less than the curvature of the cutting edges 60.

The tip 38 is advantageously tapered from wide to narrow along its longitudinal axis extending away from the support 6 for relative ease of insertion into the surgical site, as best shown in FIG. 2 for the tip 14.

Cuts 59 made by the tip 14 on a cartilage 61 is disclosed in FIG. 8. Bites 63 made by the tip 38 is disclosed in FIG. 9. Note that the bites 63 made by the tip 38 are more circular, advantageously providing a better partial meniscectomy, since the meniscal cartilage being trimmed has a curved shape.

In operation, the punch R is used in arthroscopic surgery, as best shown in FIG. 10. A fiber-optic device 62 is inserted into the knee 64 to provide an image of the surgery site in a video monitor 66. Fluid inflow 68 and outflow 70 connected to cannulas 69 and 71 provide for the clearing of tissues cut by the punch R and to distend the knee joint.

For a meniscectomy, the device R is inserted between the femur 72 and the tibia 74 to gain access to the meniscal cartilage lying therebetween. If a big suction shaver were inserted between the femur 72 and the tibia 74, it could damage the articular cartilage and this would be poor surgical technique. Therefore, the punch R advantageously makes tissue fragments that will not clog the outflow 70 or suction shaver. Additionally, the suction shaver used at this site is limited in size, making the small fragments generated by the punch R advantageously desirable.

The arrow-shaped tip 38 advantageously provides for easier penetration of the surgical site. In arthroscopy, small holes called port holes are cut with a sharp pointed scalpel. The holes are sometimes difficult to penetrate with a square tipped instrument. The arrow-shaped tip 38 advantageously penetrates the knee relatively more easily.

In doing meniscectomy, where the meniscus has a round shape, it is advantageous to take round bites when trimming about the curved-shaped meniscus. The tip 38 is not completely circular, but with basically a triangular rounded shape, whereby simply turning and angulating the punch R can provide different shapes of bites on the meniscus.

While this invention has been described as having preferred design, it is understood that it is capable of further modification, uses and/or adaptations following in general the principle of the invention and including such departures from the present disclosure as come within known or customary practice in the art to which the invention pertains, and as may be applied to the essential features set forth, and fall within the scope of the invention or the limits of the appended claims.

I claim:

1. A surgical punch for cutting body tissue, comprising:

a) an axially elongated support having first and second end portions;

b) first and second cutting jaws operably associated with said first end portion and movable between an open position and a closed position relatively toward and closely past each other in tissue-severing shearing action;

c) an actuator operably associated with said second end portion for providing relative motion between said first and second jaws;

d) said first jaw having an opening adapted to receive said second jaw in tissue-severing shearing action in the closed position, said second jaw including an outer periphery adapted to be received within said first jaw opening in the closed position, thereby to provide the tissue-severing shearing action;

e) a plurality of blades disposed within said opening for dividing said opening into a plurality of smaller through openings; and f) said second jaw cooperating with said blades when in the closed position, thereby to cut the tissue in one cutting action into smaller fragments substantially corresponding to the sizes of said smaller openings, whereby the cut fragments are adapted to be released from said cutting jaws.

2. A surgical punch as in claim 1, wherein:
a) said second jaw includes a plurality of slots adapted to receive the respective blades when said second jaw is in the closed position.

3. A surgical punch as in claim 1, wherein:
a) said blades are substantially transverse to each other.

4. A surgical punch as in claim 1, wherein:
a) said blades are substantially flush with said opening.

5. A surgical punch as in claim 1, wherein:
a) said first and second jaws are substantially rectangular in plan view.

6. A surgical punch as in claim 1, wherein:
a) said actuator includes a first handle;
b) a second handle pivotably secured to said first handle; and
c) a coupling member secured to said second jaw and said second handle for moving said second jaw between said open and closed positions relative to said first jaw.

7. A surgical punch as in claim 6, wherein:
a) said support includes a groove; and
b) said coupling member is disposed within said groove.

8. A surgical punch as in claim 1, wherein:
a) said second jaw is pivotably secured to said support.

9. A surgical punch as in claim 1, wherein:
a) said first jaw is tapered from wide to narrow along its longitudinal axis extending away from said support.

10. A surgical punch as in claim 9, wherein:
a) said first and second jaws are wider than the width of said support.

11. A surgical punch as in claim 1, wherein:
a) said first and second jaws are substantially arrow-triangular-shaped.

12. A surgical punch as in claim 11, wherein:
a) said first and second jaws each includes arcuate outer and middle portions with a first curvature and arcuate portions between said outer and middle portions with a second curvature larger than the first curvature.

13. A surgical punch as in claim 11, wherein:
a) said first jaw is tapered from wide to narrow along its longitudinal axis extending away from said support.

14. A surgical punch as in claim 11, wherein:
a) said first and second jaws each includes a middle portion wider than the width of said support.

15. A surgical punch for cutting body tissue, comprising:
a) an axially elongated support having first and second end portions;
b) first and second cutting jaws operably associated with said first end portion and movable between an open position and a closed position relatively toward and closely past each other in tissue-severing shearing action;
c) an actuator operably associated with said second end portion for actuating said second jaw relative to said first jaw;
d) said first jaw having an opening adapted to receive said second jaw in tissue-severing shearing action in the closed position, said second jaw including an outer periphery adapted to be received within said first jaw opening in the closed position, thereby to provide the tissue-severing shearing action;
e) a plurality of blades disposed substantially transversely to each other and in the direction of motion of said second jaw within said opening for dividing said opening into a plurality of smaller through openings; and
f) said second jaw including a plurality of slots adapted to receive the respective blades when said second jaw is in the closed position, thereby to cut the tissue in one cutting action into smaller fragments substantially corresponding to the sizes of said smaller openings, whereby the cut fragments are adapted to be released from said cutting jaws.

16. A surgical punch as in claim 15, wherein:
a) said first jaw is tapered from wide to narrow along its longitudinal axis extending away from said support.

17. A surgical punch as in claim 15, wherein:
a) said first jaw is wider than the width of said support.

18. A surgical punch as in claim 15, wherein:
a) said first and second jaws are substantially arrow-shaped.

19. A surgical punch as in claim 18, wherein:
a) said first and second jaws each includes arcuate outer and middle portions with a first curvature and arcuate portions between said outer and middle portions with a second curvature larger than the first curvature.

20. A surgical punch as in claim 19, wherein:
a) said first jaw is tapered from wide to narrow along its longitudinal axis extending away from said support.

21. A surgical punch as in claim 19, wherein:
a) said first and second jaws each includes a middle portion wider than the width of said support.

* * * * *